United States Patent
Welty et al.

(10) Patent No.: US 9,186,170 B2
(45) Date of Patent: Nov. 17, 2015

(54) BIDIRECTIONAL EXPANDABLE HEAD FOR ROTATIONAL ATHERECTOMY DEVICE

(75) Inventors: Ryan Welty, Blaine, MN (US); Charles A. Plowe, Hugo, MN (US); Cassandra A. Piippo, Hugo, MN (US); Todd James Bakken, Madison, WI (US); Jesse C. Darley, Madison, WI (US)

(73) Assignee: Cardiovascular Systems, Inc., St. Paul, MN (US)

( * ) Notice: Subject to any disclaimer, the term of this patent is extended or adjusted under 35 U.S.C. 154(b) by 1269 days.

(21) Appl. No.: 12/466,130

(22) Filed: May 14, 2009

(65) Prior Publication Data

US 2009/0306689 A1    Dec. 10, 2009

Related U.S. Application Data

(60) Provisional application No. 61/058,962, filed on Jun. 5, 2008.

(51) Int. Cl.
 *A61B 17/22* (2006.01)
 *A61B 17/3207* (2006.01)
 *A61B 17/32* (2006.01)

(52) U.S. Cl.
 CPC . *A61B 17/320725* (2013.01); *A61B 17/320758* (2013.01); *A61B 2017/320004* (2013.01)

(58) Field of Classification Search
 CPC ............... A61B 17/32075; A61B 17/320758; A61B 2017/230004; A61B 2017/320733; A61B 2017/320766; A61B 2017/320791; A61B 2017/320032
 USPC .................. 606/159, 167, 170, 174
 See application file for complete search history.

(56) References Cited

U.S. PATENT DOCUMENTS

| | | | |
|---|---|---|---|
| 4,043,323 A * | 8/1977 | Komiya | 600/104 |
| 4,895,560 A | 1/1990 | Papantonakos | |
| 5,030,201 A | 7/1991 | Palestrant | |
| 5,041,124 A | 8/1991 | Kensey | |
| 5,100,425 A | 3/1992 | Fischell et al. | |
| 5,158,564 A | 10/1992 | Schnepp-Pesch et al. | |

(Continued)

FOREIGN PATENT DOCUMENTS

| | | |
|---|---|---|
| JP | 2003290239 | 10/2003 |
| WO | WO02/062226 | 8/2002 |

*Primary Examiner* — Kathleen Holwerda
*Assistant Examiner* — Sarah Simpson
(74) *Attorney, Agent, or Firm* — Winthrop & Weinstine, P.A.

(57) ABSTRACT

A rotational atherectomy device that includes an expandable head that can clean a blockage from vessel larger than its rest diameter, in which the drive shaft may rotate in two opposite directions and may have different abrasive characteristics for each rotation direction. In one direction, the head may be configured for cutting and/or slicing, which may be well suited to removing particularly soft blockage material. In the other direction, the head may be configured for grinding, scraping and/or sanding, which may be well suited to removing particularly hard blockage material. The head includes one or more arms that are pivotally or hingedly attached to the drive shaft. One or more abrasive elements are disposed on or are attached to the one or more arms. The abrasive elements have a cutting feature, such as a sharpened edge that cuts like a razor blade when the drive shaft is rotated in the "cutting" direction. The abrasive elements also have a grinding feature, such as an abrasive material disposed on the abrasive element adjacent to the sharpened edge, which grinds away a blockage when the drive shaft is rotated in the "grinding" direction.

27 Claims, 8 Drawing Sheets

(56) References Cited

U.S. PATENT DOCUMENTS

| | | | |
|---|---|---|---|
| 5,192,291 A | 3/1993 | Pannek, Jr. | |
| 5,224,945 A | 7/1993 | Pannek, Jr. | |
| 5,242,461 A * | 9/1993 | Kortenbach et al. | 606/159 |
| 5,308,354 A | 5/1994 | Zacca et al. | |
| 5,318,576 A | 6/1994 | Plassche, Jr. et al. | |
| 5,376,100 A | 12/1994 | Lefebvre | |
| 5,728,123 A | 3/1998 | Lemelson et al. | |
| 5,766,192 A | 6/1998 | Zacca | |
| 5,817,095 A | 10/1998 | Smith | |
| 5,833,650 A | 11/1998 | Imran | |
| 6,096,054 A | 8/2000 | Wyzgala et al. | |
| 6,132,444 A * | 10/2000 | Shturman et al. | 606/159 |
| 6,416,526 B1 | 7/2002 | Wyzgala et al. | |
| 6,436,111 B1 * | 8/2002 | Kadavy et al. | 606/159 |
| 6,503,261 B1 * | 1/2003 | Bruneau et al. | 606/159 |
| 6,565,588 B1 | 5/2003 | Clement et al. | |
| 6,596,005 B1 | 7/2003 | Kanz et al. | |
| 6,685,718 B1 | 2/2004 | Wyzgala et al. | |
| 6,726,690 B2 | 4/2004 | Eckman | |
| 6,800,083 B2 * | 10/2004 | Hiblar et al. | 606/159 |
| 6,800,085 B2 | 10/2004 | Selmon et al. | |
| 6,818,001 B2 | 11/2004 | Wulfman et al. | |
| 7,252,674 B2 | 8/2007 | Wyzgala et al. | |
| 7,303,531 B2 * | 12/2007 | Lee et al. | 600/564 |
| 7,344,546 B2 | 3/2008 | Wulfman et al. | |
| 2002/0026145 A1 | 2/2002 | Bagaoisan et al. | |
| 2002/0052638 A1 | 5/2002 | Zadno-Azizi | |
| 2002/0077638 A1 | 6/2002 | Kadavy et al. | |
| 2003/0199889 A1 | 10/2003 | Kanz et al. | |
| 2003/0208222 A1 | 11/2003 | Zadno-Azizi | |
| 2004/0015150 A1 | 1/2004 | Zadno-Azizi | |
| 2005/0149084 A1 * | 7/2005 | Kanz et al. | 606/159 |
| 2005/0277971 A1 * | 12/2005 | Melkent et al. | 606/180 |
| 2006/0200074 A1 | 9/2006 | Zadno-Azizi | |
| 2006/0200075 A1 | 9/2006 | Zadno-Azizi | |
| 2006/0200191 A1 | 9/2006 | Zadno-Azizi | |

\* cited by examiner

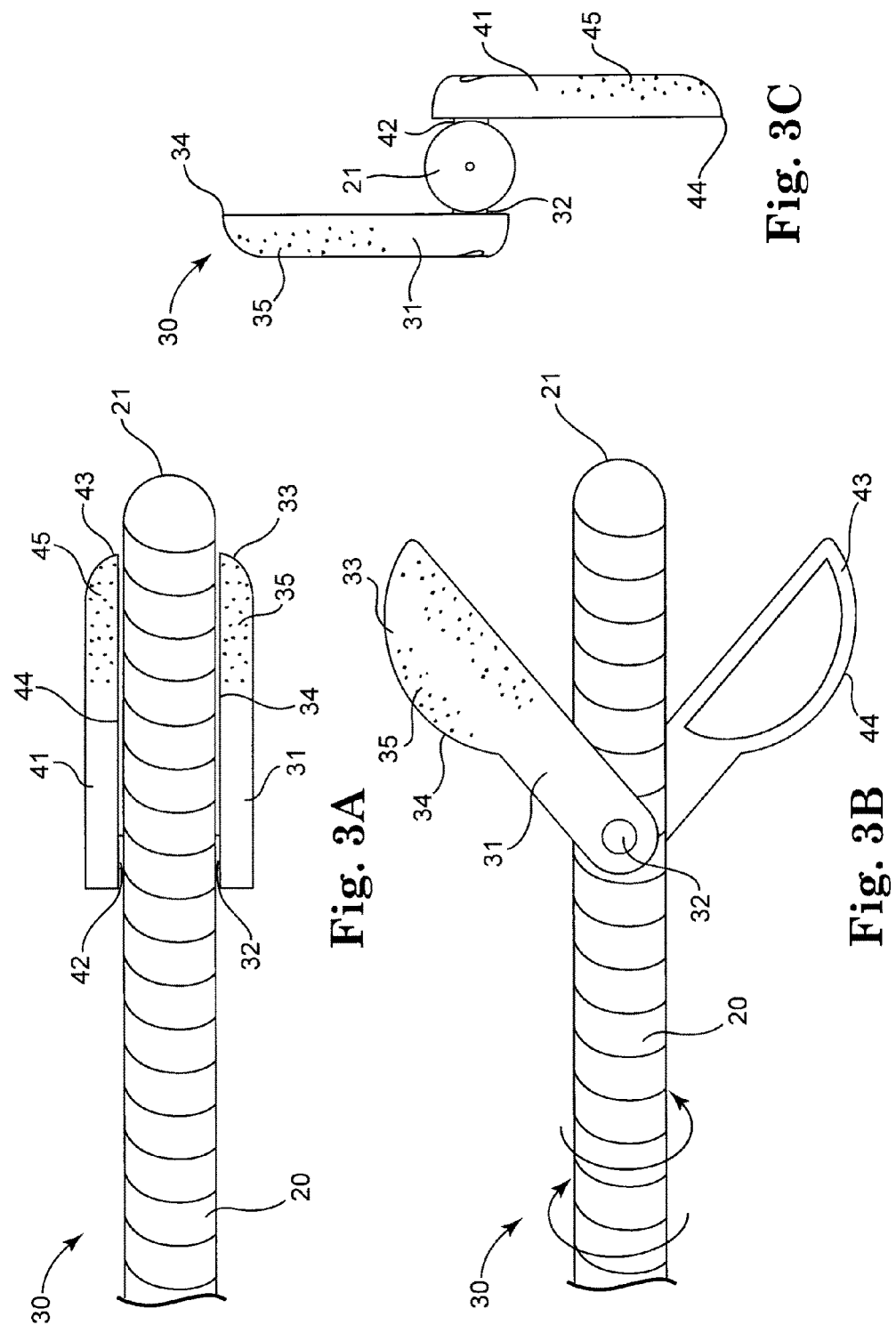

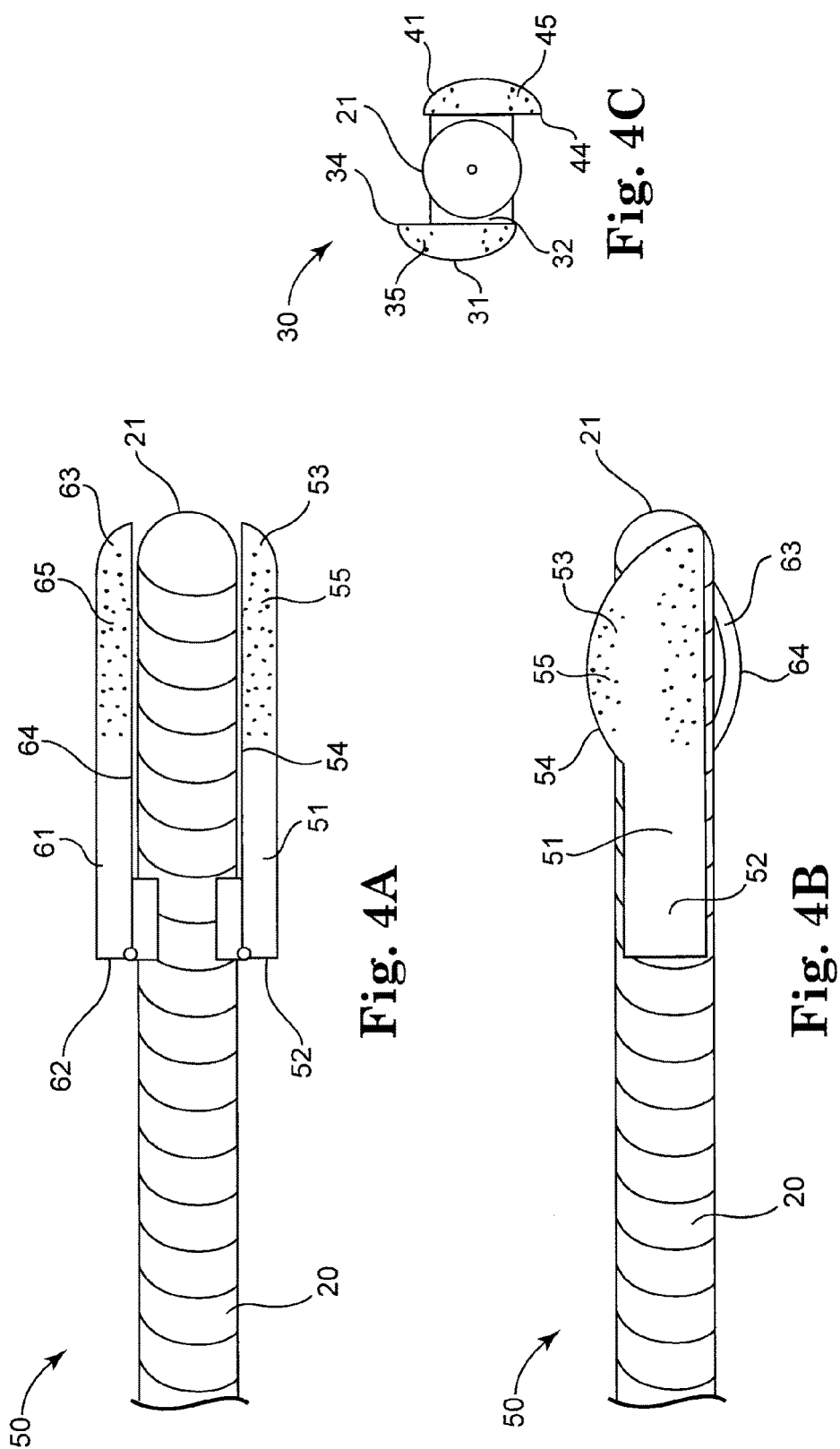

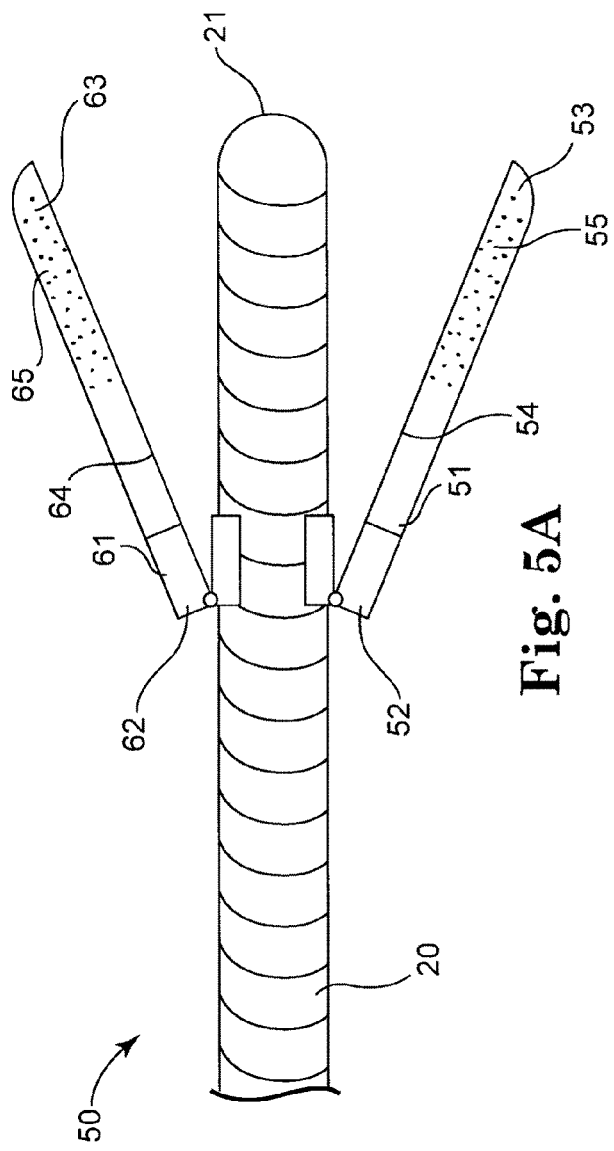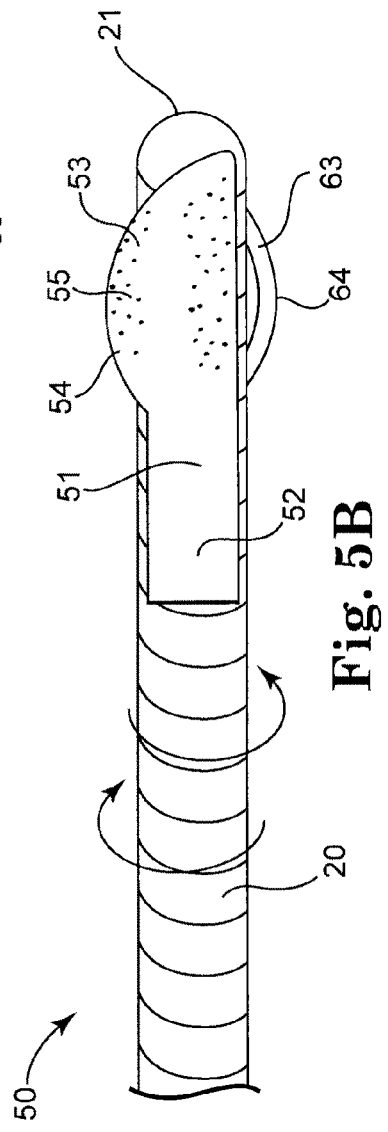

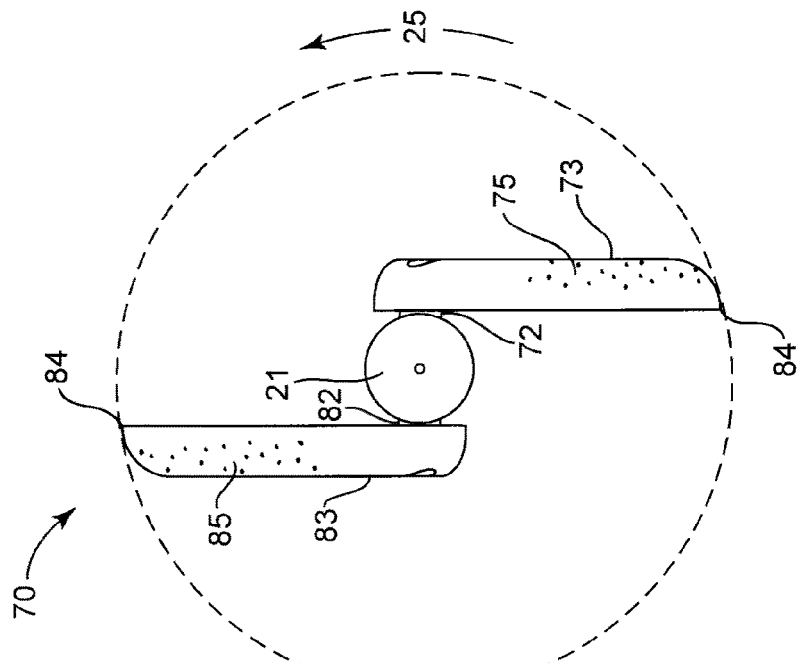
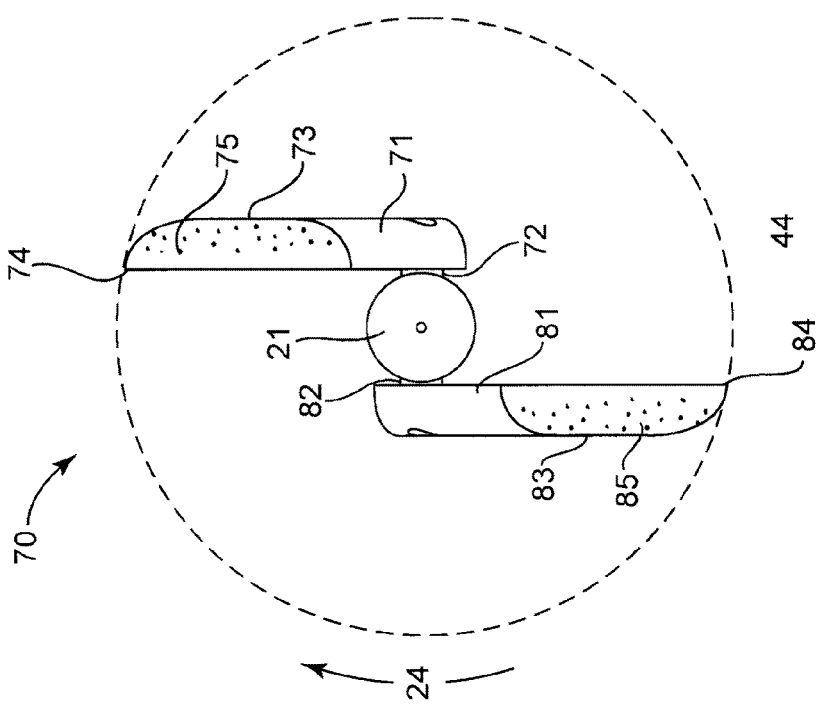

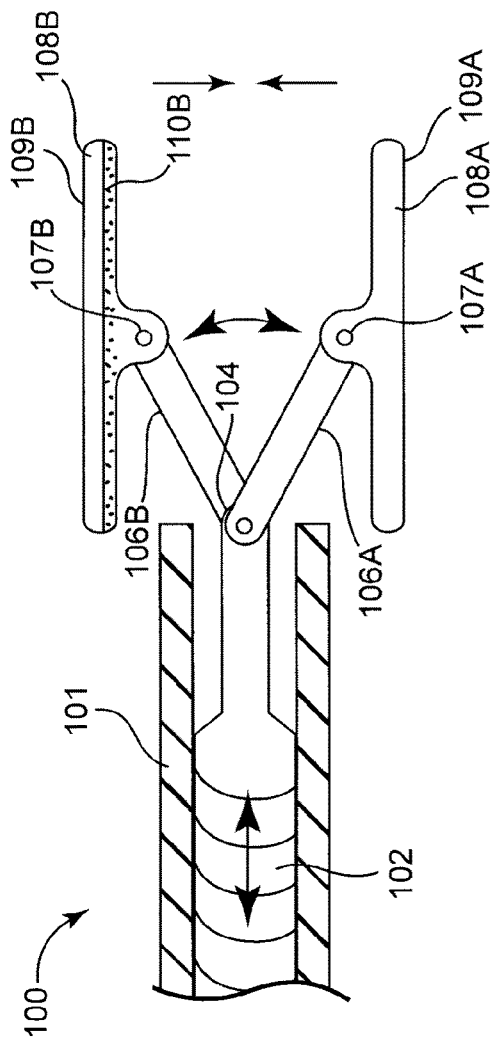
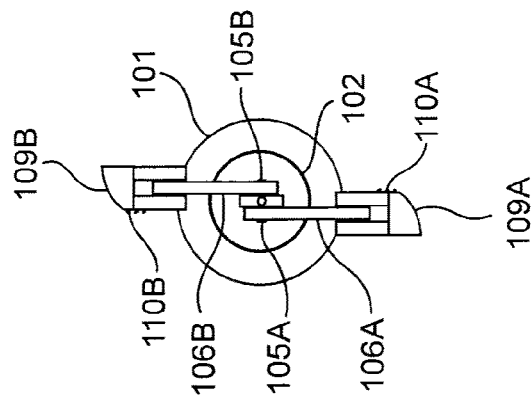
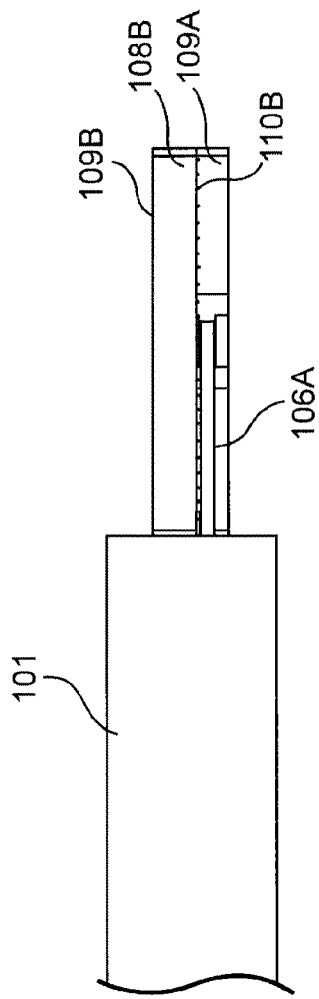

BIDIRECTIONAL EXPANDABLE HEAD FOR ROTATIONAL ATHERECTOMY DEVICE

CROSS-REFERENCE TO RELATED APPLICATIONS

The present application claims priority to provisional application No. 61/058,962, filed on Jun. 5, 2008 under the title, "BIDIRECTIONAL EXPANDABLE HEAD FOR ROTATIONAL ATHERECTOMY DEVICE", the contents of which are incorporated by reference herein.

STATEMENT REGARDING FEDERALLY SPONSORED RESEARCH OR DEVELOPMENT

Not Applicable

BACKGROUND OF THE INVENTION

1. Field of the Invention

The present invention is directed to expandable abrasive/cutting heads for rotation atherectomy devices.

2. Description of the Related Art

Atherectomy is a non-surgical procedure to open blocked coronary arteries or vein grafts by using a device on the end of a catheter to cut or shave away atherosclerotic plaque (a deposit of fat and other substances that accumulate in the lining of the artery wall). For the purposes of this application, the term "abrading" is used to describe the grinding and/or scraping action of such an atherectomy head.

Atherectomy is performed to restore the flow of oxygen-rich blood to the heart, to relieve chest pain, and to prevent heart attacks. It may be done on patients with chest pain who have not responded to other medical therapy and on certain of those who are candidates for balloon angioplasty (a surgical procedure in which a balloon catheter is used to flatten plaque against an artery wall) or coronary artery bypass graft surgery. It is sometimes performed to remove plaque that has built up after a coronary artery bypass graft surgery.

Atherectomy uses a rotating shaver or other device placed on the end of a catheter to slice away or destroy plaque. At the beginning of the procedure, medications to control blood pressure, dilate the coronary arteries, and prevent blood clots are administered. The patient is awake but sedated. The catheter is inserted into an artery in the groin, leg, or arm, and threaded through the blood vessels into the blocked coronary artery. The cutting head is positioned against the plaque and activated, and the plaque is ground up or suctioned out.

The types of atherectomy are rotational, directional, and transluminal extraction. Rotational atherectomy uses a high speed rotating shaver to grind up plaque. Directional atherectomy was the first type approved, but is no longer commonly used; it scrapes plaque into an opening in one side of the catheter. Transluminal extraction coronary atherectomy uses a device that cuts plaque off vessel walls and vacuums it into a bottle. It is used to clear bypass grafts.

Performed in a cardiac catheterization lab, atherectomy is also called removal of plaque from the coronary arteries. It can be used instead of, or along with, balloon angioplasty. Atherectomy is successful about 95% of the time. Plaque forms again in 20-30% of patients.

Several devices have been disclosed that perform rotational atherectomy. For instance, U.S. Pat. No. 5,360,432, issued on Nov. 1, 1994 to Leonid Shturman, and titled "Abrasive drive shaft device for directional rotational atherectomy" discloses an abrasive drive shaft atherectomy device for removing stenotic tissue from an artery, and is incorporated by reference herein in its entirety. The device includes a rotational atherectomy apparatus having a flexible, elongated drive shaft having a central lumen and a segment, near its distal end, coated with an abrasive material to define an abrasive segment. At sufficiently high rotational speeds, the abrasive segment expands radially, and can sweep out an abrading diameter that is larger than its rest diameter. In this manner, the atherectomy device may remove a blockage that is larger than the catheter itself. Use of an expandable head is an improvement over atherectomy devices that use non-expandable heads; such non-expandable devices typically require removal of particular blockages in stages, with each stage using a differently-sized head.

In the years since the '432 patent, there has been a significant effort to improve the expandable head, with many devices using centrifugal force or other devices to drive portions of the abrasive head radially outward at high rotational speeds.

For all of these devices, the abrasive head includes an abrasive that has a single set of properties. For instance, an abrasive burr may include abrasive particles of a particular size or a particular distribution of sizes. Or, a particular head may have a cutting effect on the blockage, rather than a grinding effect.

There may be some instances when a practitioner requires two different abrading heads for a single blockage. For instance, a particular blockage may have hard plaques, which may be effectively removed by sanding or scraping, as well as soft lesions, which may be effectively removed by slicing or cutting. The cutting head may have different properties than the scraping head.

If a practitioner wants to use a first abrasive, then use a second abrasive having different properties than the first abrasive, the practitioner must remove the device with the first abrasive, then insert the device with the second abrasive. This removal of one catheter and insertion of another catheter is time-consuming, inconvenient, expensive, and requires additional parts that must be manufactured, shipped, inventoried, and maintained with the atherectomy device.

Accordingly, there exists a need for a rotational atherectomy abrading head that can exhibit two different sets of properties. Such a head would reduce the expense, time and burden of using additional heads for the rotational atherectomy device.

BRIEF SUMMARY OF THE INVENTION

An embodiment is a rotational atherectomy apparatus for abrading tissue, comprising: a flexible, elongated, rotatable drive shaft having a proximal end and a distal end opposite the proximal end, the drive shaft being rotatable in a cutting direction and in a grinding direction opposite the cutting direction; an expandable abrasive element disposed proximate the distal end of the drive shaft, the abrasive element further comprising: a cutting element expandably exposed to tissue when the drive shaft is rotated in the cutting direction at a high rotational speed; a grinding element expandably exposed to tissue when the drive shaft is rotated in the grinding direction at a high rotational speed; and a rotational diameter that is expandably greater than its rest diameter.

Another embodiment is a rotational atherectomy apparatus, comprising: a flexible, elongated, rotatable drive shaft having a proximal end and a distal end opposite the proximal end, the drive shaft being rotatable in a cutting direction and in a grinding direction opposite the cutting direction; a first arm pivotally attached to the drive shaft at a first drive shaft anchor point near the distal end of the drive shaft, the first arm being pivotable in a first plane tangential to the drive shaft at the first drive shaft anchor point; the first arm having a first arm free end that leads the first drive shaft anchor point when the drive shaft is rotated in the cutting direction and trails the first drive shaft anchor point when the drive shaft is rotated in the grinding direction; the first arm free end having a first cutting feature on a leading edge of the first arm free end as the drive shaft is rotated in the cutting direction; and the first arm free end having a first grinding feature adjacent to the first cutting feature and leading the first cutting feature as the drive shaft is rotated in the grinding direction.

Yet another embodiment is a rotational atherectomy apparatus, comprising: a flexible, elongated, rotatable drive shaft having a proximal end and a distal end opposite the proximal end, the drive shaft being rotatable in a cutting direction and in a grinding direction opposite the cutting direction; a first arm hingedly attached to the drive shaft at a first drive shaft anchor point near the distal end of the drive shaft, the first arm being pivotable in a first plane that includes a rotational axis of the drive shaft; the first arm having a first arm free end that extends radially away from the drive shaft at high drive shaft rotational speeds; the first arm free end having a first cutting feature on a leading edge of the first arm free end as the drive shaft is rotated in the cutting direction; and the first arm free end having a first grinding feature adjacent to the first cutting feature and leading the first cutting feature as the drive shaft is rotated in the grinding direction.

Still another embodiment is a rotational atherectomy apparatus, comprising: a flexible, elongated, rotatable drive shaft having a proximal end and a distal end opposite the proximal end, the drive shaft being rotatable in a cutting direction and in a grinding direction opposite the cutting direction; a first arm pivotally attached to the drive shaft at a first drive shaft anchor point near the distal end of the drive shaft, the first arm being pivotable in a first plane tangential to the drive shaft at the first drive shaft anchor point; the first arm having a first arm free end that leads the first drive shaft anchor point when the drive shaft is rotated in the cutting direction and trails the first drive shaft anchor point when the drive shaft is rotated in the grinding direction; a first abrasive element pivotally attached to the first arm, the first abrasive element being pivotable in a plane parallel to the first plane; the first abrasive element having a first cutting feature on a leading edge of the first abrasive element as the drive shaft is rotated in the cutting direction; and the first abrasive element having a first grinding feature adjacent to the first cutting feature and leading the first cutting feature as the drive shaft is rotated in the grinding direction.

BRIEF DESCRIPTION OF THE SEVERAL VIEWS OF THE DRAWINGS

FIGS. 3A, 3B and 3C are top, front and right-side plan drawings, respectively, of the atherectomy head of FIGS. 2A, 2B and 2C, at high rotational speeds.

FIGS. 4A, 4B and 4C are top, front and right-side plan drawings, respectively, of an atherectomy head, at rest or low rotational speeds.

FIGS. 5A, 5B and 5C are top, front and right-side plan drawings, respectively, of the atherectomy head of FIGS. 4A, 4B and 4C, at high rotational speeds.

FIG. 6 is a plan drawing of an atherectomy head, with the drive shaft rotating in the cutting direction, viewed from the distal end of the drive shaft.

FIG. 7 is a plan drawing of the atherectomy head of FIG. 6, with the drive shaft rotating in the grinding direction, viewed from the distal end of the drive shaft.

FIGS. 8A, 8B and 8C are top, front and right-side plan drawings, respectively, of an atherectomy head, at high rotational speeds.

DETAILED DESCRIPTION OF THE INVENTION

Figure 1:
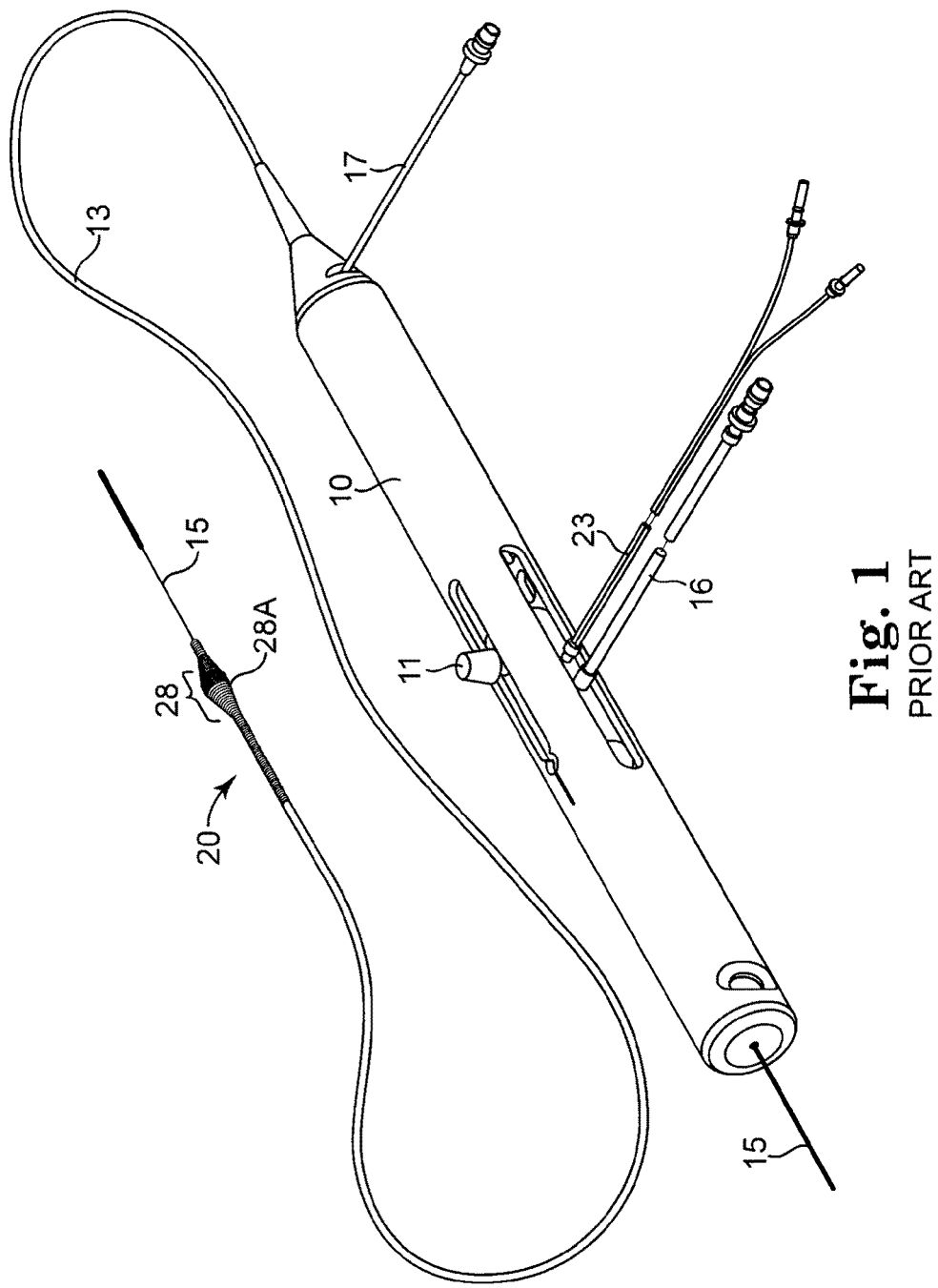
FIG. 1 is a schematic drawing of a typical rotational atherectomy device.

A rotational atherectomy device is disclosed that includes an expandable head that can clean a blockage from vessel larger than its rest diameter, in which the drive shaft may rotate in two opposite directions and may have different abrasive characteristics for each rotation direction. In one direction, the head may be configured for cutting and/or slicing, which may be well suited to removing particularly soft blockage material. In the other direction, the head may be configured for grinding, scraping and/or sanding, which may be well suited to removing particularly hard blockage material. The head includes one or more arms that are pivotally or hingedly attached to the drive shaft. One or more abrasive elements are disposed on or are attached to the one or more arms. The abrasive elements have a cutting feature, such as a sharpened edge that cuts like a razor blade when the drive shaft is rotated in the "cutting" direction. The abrasive elements also have a grinding feature, such as an abrasive material disposed on the abrasive element adjacent to the sharpened edge, which grinds away a blockage when the drive shaft is rotated in the "grinding" direction.

The above paragraph is merely a summary, and should not be construed as limiting in any way. While the invention is amenable to various modifications and alternative forms, specifics thereof are shown by way of example in the drawings and described in detail herein. It should be understood, however, that the intention is not to limit the invention to the particular embodiments described. On the contrary, the intention is to cover all modifications, equivalents, and alternatives falling within the spirit and scope of the invention.

FIG. 1 is a schematic drawing of a typical rotational atherectomy device. The device includes a handle portion 10, an elongated, flexible drive shaft 20 having an abrasive section 28 comprising an eccentric enlarged diameter section 28A, and an elongated catheter 13 extending distally from the handle portion 10. The drive shaft 20 and its eccentric enlarged diameter section 28 are constructed from helically coiled wire. The catheter 13 has a lumen in which most of the length of the drive shaft 20 is disposed, except for the enlarged diameter section 28A and a short section distal to the enlarged diameter section 28. The drive shaft 20 also contains an inner lumen, permitting the drive shaft 20 to be advanced and rotated over a guide wire 15. A fluid supply line 17 may be provided for introducing a cooling and lubricating solution (typically saline or another biocompatible fluid) into the catheter 13.

The handle 10 desirably contains a turbine (or similar rotational drive mechanism) for rotating the drive shaft 20 at high speeds. The handle 10 typically may be connected to a power source, such as compressed air delivered through a tube 16. A pair of fiber optic cables 23 may also be provided for monitoring the speed of rotation of the turbine and drive shaft 20. Details regarding such handles and associated instrumentation are well known in the industry, and are described, e.g., in U.S. Pat. No. 5,314,407, issued to Auth. The handle 10 also desirably includes a control knob 11 for advancing and retracting the turbine and drive shaft 20 with respect to the catheter 13 and the body of the handle.

The present application is directed mainly to an abrasive head design, which may improve upon the eccentric enlarged diameter section 28 of FIG. 1. In this respect, many or all of the other elements of the known atherectomy device of FIG. 1 may be used with the present disclosed head design, including the catheter 13, the guide wire 15, and the handle 10 along with its controls and its inputs and outputs. The helically coiled drive shaft 20 may be used as well for the present disclosure, noting that the eccentric enlarged diameter section 28 of FIG. 1 may be replaced by the abrasive element or elements described in detail below.

Figure 2C:
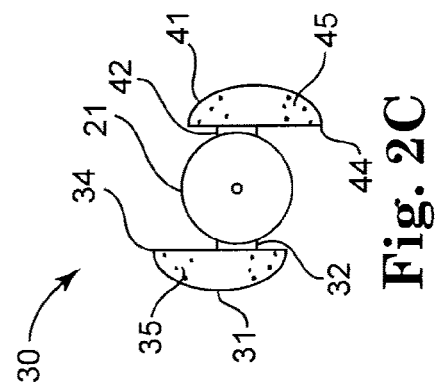
FIGS. 2A, 2B and 2C are top, front and right-side plan drawings, respectively, of an atherectomy head, at rest or low rotational speeds.
Figure 2A:
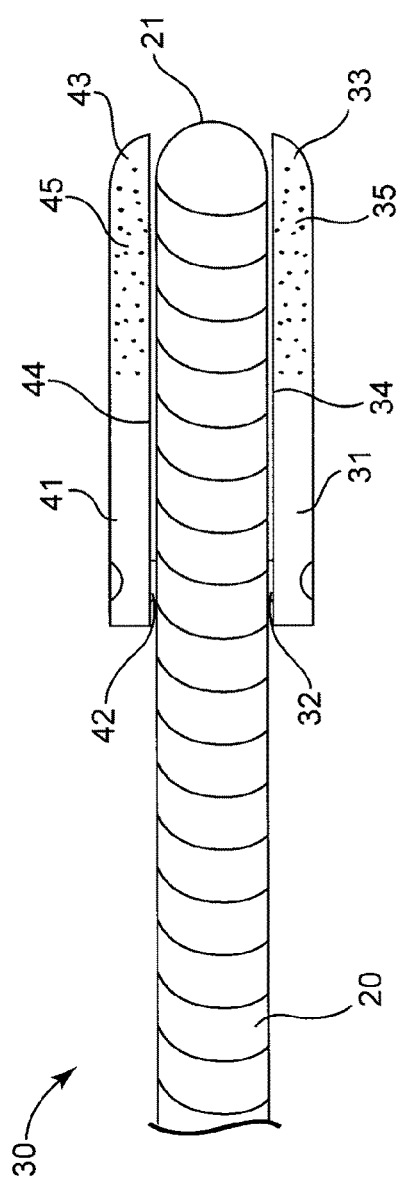
Figure 2B:
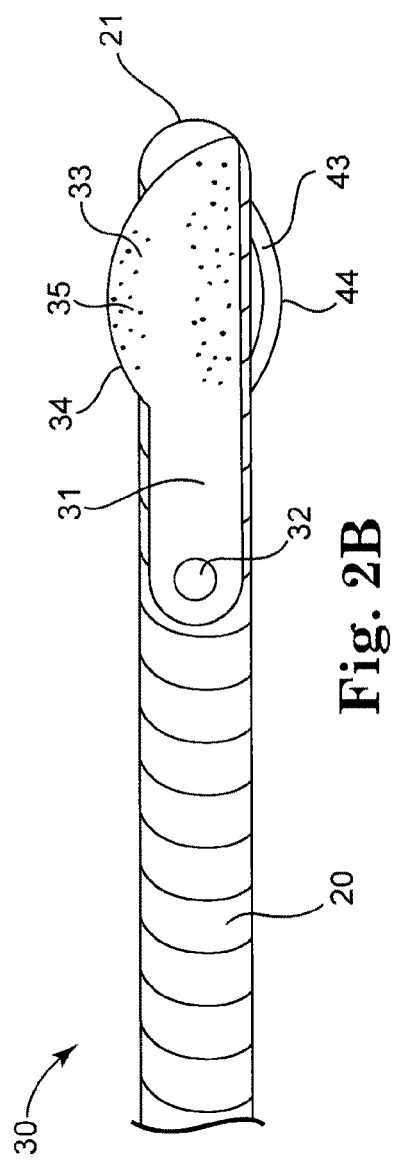

FIGS. 2A, 2B and 2C are top, front and right-side plan drawings, respectively, of an atherectomy head 30, at rest or low rotational speeds.

The drive shaft 20 may be made from a helically coiled wire, terminating at a distal end 21. The distal end 21 may be rounded, may be tapered, may be left square, or may include an optional cap that terminates the drive shaft and prevents damage to the vessel being cleaned. The distal end 21 also includes a hole that can accommodate the guide wire of the atherectomy device. Optionally, the distal end 21 may include abrasive material that may be used to start a pilot hole in the blockage, from proximal to distal portions of the blockage.

Alternatively, the drive shaft may be made from more than one wire, such as two wires, three wires, five wires, ten wires, fifteen wires, or any other suitable number of wires. For the multiple-wire drive shaft, the wires are all interwoven in the helical coil.

The atherectomy head 30 includes a pair of arms 31 and 41 that are pivotally attached to the drive shaft at drive shaft anchor points 32 and 42, respectively, and have free ends 33 and 43, respectively. The anchor points 32 and 42 are near the distal end 21 of the drive shaft 20. The arms 31 and 41 are mounted so that they may pivot in planes tangential to the drive shaft at drive shaft anchor points 32 and 42. In other words, if each arm 31 and 41 were to pivot around a line, each line would be perpendicular to the drive shaft rotation axis and would intersect the drive shaft rotation axis.

In some applications, the drive shaft anchor points 32 and 42 are directly opposite each other on the drive shaft 20. In other applications, the drive shaft anchor points 32 and 42 are both located on one side of the drive shaft. In some applications, there may be only one arm. In other applications, there may be more than two arms, optionally located equidistantly around the drive shaft. In some of these multi-arm applications, the anchor points are all located the same distance away from the distal end 21 of the drive shaft 20. In other of these multi-arm applications, one or more of the anchor points is located a different distance away from the distal end 21 of the drive shaft 20 than one or more of the other anchor points.

In some applications, the arms 31 and 41 have equal masses, so that the combined center of mass of the two arms lies on the rotational axis of the drive shaft. In other applications, the arms 31 and 41 have different masses, so that their combined center of mass is laterally displaced from the rotational axis of the drive shaft. In still other applications, the drive shaft itself may have one or more enlarged portions in the vicinity of the anchor points.

At rest or at low rotational speeds, as in FIG. 2, the arms 31 and 41 may be oriented generally parallel to the drive shaft. This generally parallel orientation may help reduce the cross-sectional size of the atherectomy head 30, so that it may fit within a relatively small catheter 13 during insertion, positioning, and removal. For instance, with the arms 31 and 41 in their rest position, the atherectomy head 30 may fit with a size 6 or 7 French catheter (i.e., a 2 or 2.33 mm-diameter catheter), although other suitable sizes may be used as well.

The arms may include an optional feature to ensure that this rest position lies generally parallel to the drive shaft; such as a spring or other suitable orienting feature. In addition, using spring-loaded arms may allow a nearly constant force to be exerted against the wall of the vessel, and may even allow for differential cutting and/or grinding.

FIGS. 3A, 3B and 3C are top, front and right-side plan drawings, respectively, of the atherectomy head 30 of FIGS. 2A, 2B and 2C, at high rotational speeds. At these high rotational speeds, the arms 31 and 41 become extended away from the drive shaft 20. The arm extension may occur due to centrifugal force, or due to any suitable actuating force.

The free ends 33 and 43 of the arms 31 and 41 may include one or more abrading features for cutting at a blockage in the vessel, and one or more abrading features for grinding at a blockage in the vessel. The distinction between cutting and grinding may not be merely academic; the type of abrading may be matched to a particular hardness of blockage material, so that cutting may suit a particular hardness and grinding may suit a different hardness. In some applications, cutting and/or slicing may be well suited to particularly soft blockage material, while grinding, scraping and/or sanding may be well suited to particularly hard blockage material.

The free ends 33 and 43 of the arms 31 and 41 include cutting edges 34 and 44, respectively. In some applications, the cutting features may be a blade or multiple blades along one or more edges of the free ends 33 and 43 of the arms 31 and 41, respectively. In some embodiments, each blade may include arm material formed with a right angle and/or an acute angle, so that when the drive shaft is rotated in the so-called "cutting direction" 24, a blade is passed over the blockage and a small portion of the blockage is shaved off. In practice, removal of the blockage may require many passes of the blade over the blockage, which may be accomplished in a relatively short amount of time due to the relatively high drive shaft rotation speed. The orientation of the cutting edges 34 and 44 on the free ends 33 and 43 of the arms 31 and 41 are seen a bit more clearly in several of the following figures, which show the arms 31 and 41 in outstretched or extended positions at relatively high rotation speeds.

The free ends 33 and 43 of the arms 31 and 41 also include grinding edges. The grinding edges may include abrasive grit or other abrasive material 35 and 45 disposed on an exterior face of the free ends 33 and 43 of the arms 31 and 41. In some applications, the abrasive material may be dragged across the vessel blockage just prior to the grinding edge passing over the blockage, when the drive shaft is rotated in a so-called "grinding direction" 25, which is in the opposite direction as the "cutting direction" 24.

Note that the so-called "cutting edges" may be the same physical surfaces as the so-called "grinding edges", where the blade-like characteristic of the edge may cut when the drive shaft is rotated in the cutting direction, but may simply pass over the blockage material when the drive shaft is rotated in the grinding direction. This edge may be analogous to the blade in a shaver, which provides a close shave when passed over skin in one orientation, but does little when passed over skin in the opposite orientation.

In some applications, the so-called "cutting feature" may be the cutting edge itself, and the so-called "grinding feature" may be the abrasive material located on the free end of the arm, adjacent to the cutting edge. In these applications, the so-called "grinding edge" may be the same physical surface as the cutting edge, where, like a razor blade, the edge shaves material off the blockage when passed over the blockage in one orientation (the cutting direction) but has little effect when passed over the blockage in the other orientation (the grinding direction). In these applications, the so-called "grinding" occurs from the abrasive material on the free end of the arm, which may located adjacent to the cutting/grinding edge itself. In these applications, the grinding feature may be considered to be "on" the grinding edge, even though the grinding feature may be an abrasive material disposed on the free end of the arm, adjacent to the grinding edge and trailing the grinding edge when the drive shaft is rotated in the grinding direction.

The atherectomy head 30 may include optional motion limiters on one or both arms 31 and 41. For instance, an optional motion limiter may prevent one or both arms 31 and 41 from extending completely perpendicular to the drive shaft, and may allow movement only to a particular angle, such as 45 degrees, 60 degrees, or any other suitable angle less than 90 degrees. As another example, an optional motion limiter may allow movement of one or both arms 31 and 41 to only one side of the drive shaft, thereby ensuring that arm 31 moves "up" and arm 41 moves "down", as in FIG. 3. The optional motion limiters may be included with the anchor points, the drive shaft, or the arms themselves.

In some applications, the arms 31 and 41 each include a scoop-like shape to the free end, where the scoop includes abrasive material on its outer surface and has a sharpened edge that acts as a blade-like structure when the drive shaft is rotated in the cutting direction. In some applications, the scoops may be a pair of hemispherical cups that nest together and pivot about an axle at a distance from their distal tips. Optionally, there may be extensions of the cups on the proximal side of the axle to allow for a scissor-like blade structure. In other applications, the arms 31 and 41 may include a pair or multitude of blades with central pivots the nest together in parallel, where a linkage connects them to a central pivot. In still other applications, the arms 31 and 41 may include a pair of flat blades similar to scissor blades but with their outer edges sharpened, which pivot about an axle at a distance from their distal tips.

An alternative design for the atherectomy head uses arms that hinge to the drive shaft and can expand radially outward during high drive shaft rotational speeds, rather than arms that pivot as in FIGS. 2 and 3. These hinged arms are shown in FIGS. 4 and 5.

Figure 5C:
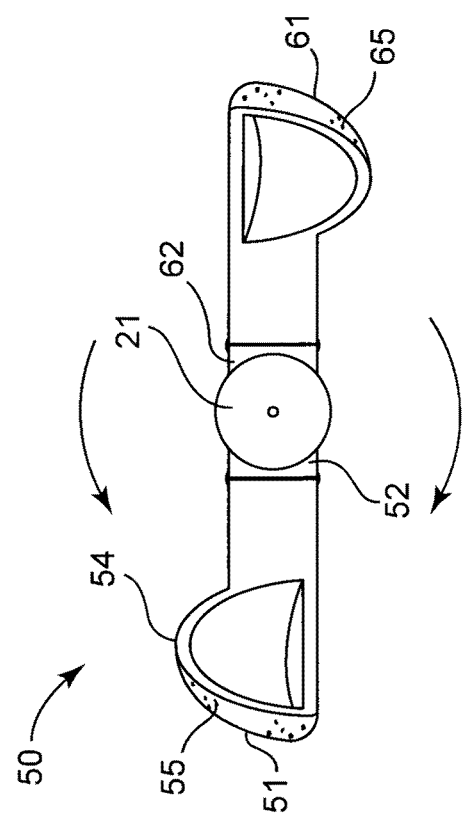

FIGS. 4A, 4B and 4C are top, front and right-side plan drawings, respectively, of an atherectomy head 50, at rest or low rotational speeds. FIGS. 5A, 5B and 5C are top, front and right-side plan drawings, respectively, of the atherectomy head 50 of FIGS. 4A, 4B and 4C, at high rotational speeds.

The atherectomy head 50 includes a pair of arms 51 and 61 that are hingedly attached to the drive shaft at hinges 52 and 62, respectively, and have free ends 53 and 63, respectively. The hinges 52 and 62 are near the distal end 21 of the drive shaft 20. In some applications, the arms 51 and 61 are mounted so that they may move in a plane that includes the rotational axis of the drive shaft.

In some applications, the hinges 52 and 62 are directly opposite each other on the drive shaft 20. In other applications, the drive shaft anchor points 52 and 62 are both located on one side of the drive shaft. In some applications, there may be only one arm. In other applications, there may be more than two arms, optionally located equidistantly around the drive shaft. In some of these multi-arm applications, the anchor points are all located the same distance away from the distal end 21 of the drive shaft 20. In other of these multi-arm applications, one or more of the anchor points is located a different distance away from the distal end 21 of the drive shaft 20 than one or more of the other anchor points.

In some applications, the arms 51 and 61 have equal masses, so that the combined center of mass of the two arms lies on the rotational axis of the drive shaft. In other applications, the arms 51 and 61 have different masses, so that their combined center of mass is laterally displaced from the rotational axis of the drive shaft. In still other applications, the drive shaft itself may have one or more enlarged portions in the vicinity of the anchor points.

At rest or at low rotational speeds, as in FIG. 4, the arms 51 and 61 may be oriented generally parallel to the drive shaft. The arms may include an optional feature to ensure that this rest position lies generally parallel to the drive shaft; such as a spring or other suitable orienting feature. This generally parallel orientation may help reduce the cross-sectional size of the atherectomy head 50, so that it may fit within a relatively small catheter 13 during insertion, positioning, and removal. For instance, with the arms 51 and 61 in their rest position, the atherectomy head 50 may fit with a size 6 or 7 French catheter (i.e., a 2 or 2.33 mm-diameter catheter), although other suitable sizes may be used as well.

At sufficiently high rotational speeds, the arms 51 and 61 become extended away from the drive shaft 20. The arm extension may occur due to centrifugal force, or due to any suitable actuating force.

The free ends 53 and 63 of the arms 51 and 61 may include one or more abrading features for cutting at a blockage in the vessel, and one or more abrading features for grinding at a blockage in the vessel.

The free ends 53 and 63 of the arms 51 and 61 include cutting edges 54 and 64, respectively. In some applications, the cutting features may be a blade or multiple blades along one or more edges of the free ends 53 and 63 of the arms 51 and 61, respectively. In some embodiments, each blade may include arm material formed with a right angle and/or an acute angle, so that when the drive shaft is rotated in the so-called "cutting direction" 24, a blade is passed over the blockage and a small portion of the blockage is shaved off. In practice, removal of the blockage may require many passes of the blade over the blockage, which may be accomplished in a relatively short amount of time due to the relatively high drive shaft rotation speed. The orientation of the cutting edges 54 and 64 on the free ends 53 and 63 of the arms 51 and 61 are seen a bit more clearly in several of the following figures, which show the arms 51 and 61 in outstretched or extended positions at relatively high rotation speeds.

The free ends 53 and 63 of the arms 51 and 61 also include grinding edges. The grinding edges may include abrasive grit or other abrasive material 55 and 65 disposed on an exterior face of the free ends 53 and 63 of the arms 51 and 61. In some applications, the abrasive material may be dragged across the vessel blockage just prior to the grinding edge passing over the blockage, when the drive shaft is rotated in a so-called "grinding direction" 25, which is in the opposite direction as the "cutting direction" 24.

Note that the so-called "cutting edges" may be the same physical surfaces as the so-called "grinding edges", where the blade-like characteristic of the edge may cut when the drive shaft is rotated in the cutting direction, but may simply pass over the blockage material when the drive shaft is rotated in the grinding direction. This edge may be analogous to the blade in a shaver, which provides a close shave when passed over skin in one orientation, but does little when passed over skin in the opposite orientation.

In some applications, the so-called "cutting feature" may be the cutting edge itself, and the so-called "grinding feature"

may be the abrasive material located on the free end of the arm, adjacent to the cutting edge. In these applications, the so-called "grinding edge" may be the same physical surface as the cutting edge, where, like a razor blade, the edge shaves material off the blockage when passed over the blockage in one orientation (the cutting direction) but has little effect when passed over the blockage in the other orientation (the grinding direction). In these applications, the so-called "grinding" occurs from the abrasive material on the free end of the arm, which may located adjacent to the cutting/grinding edge itself. In these applications, the grinding feature may be considered to be "on" the grinding edge, even though the grinding feature may be an abrasive material disposed on the free end of the arm, adjacent to the grinding edge and trailing the grinding edge when the drive shaft is rotated in the grinding direction.

The atherectomy head 50 may include optional motion limiters on one or both arms 51 and 61. For instance, an optional motion limiter may prevent one or both arms 51 and 61 from extending completely perpendicular to the drive shaft, and may allow movement only to a particular angle, such as 45 degrees, 60 degrees, or any other suitable angle less than 90 degrees. The optional motion limiters may be included with the hinges, the drive shaft, or the arms themselves.

Referring back to FIGS. 2 and 3, the atherectomy head 30 implicitly assumes that the arms 31 and 41 extend in only one direction away from the drive shaft, so that the arms 31 and 41 "lead" the drive shaft anchor points 32 and 42 when the drive shaft is rotated in the cutting direction 24, and "trail" the drive shaft anchor points 32 and 42 when the drive shaft is rotated in the grinding direction 25.

In practice, there may be an atherectomy head 70 that has arms 71 and 81 that "trail" the anchor points 72 and 82, when the drive shaft is rotated in either direction. For instance, FIG. 6 is a plan drawing of an atherectomy head 70 with the drive shaft rotating in the cutting direction 24, viewed from the distal end 21 of the drive shaft, and FIG. 7 is a plan drawing of the atherectomy head 70 of FIG. 6, with the drive shaft rotating in the grinding direction 25, viewed from the distal end 21 of the drive shaft. The head 70 has arms 71 and 81 with free ends 73 and 83 having cutting features 74 and 84 and grinding features 75 and 85; all are analogous in function to the features of FIGS. 2 and 3.

FIGS. 8A, 8B and 8C are top, front and right-side plan drawings, respectively, of an atherectomy head 100, at relatively high rotational speeds.

The atherectomy head 100 is typically moved through a patient's vasculature within a catheter 101, so that the head and drive shaft 102 do not cause any damage to the vessels during insertion or extraction. For this particular head design, the catheter 101 is shown in the figures, and it will be understood that similar-functioning catheters may also be used with the head designs of FIGS. 2-5.

The drive shaft 102 has a proximal end located at or near the operator, external to the patient's body, and a distal end 104 that extends to or near the end of the catheter 101. In some applications, the drive shaft 102 includes one or more helically coiled wires, although any suitable torque-transmitting structure may be used. In some applications, the distal end 104 of the drive shaft includes a hole that can accommodate a guide wire (not shown). In some applications, the drive shaft 102 may include an optional taper 103 that reduces the diameter of the helical coils in the vicinity of the distal end 104. The function of this optional taper 103 is described below.

The distal end 104 of the drive shaft 102 includes a pair of hinges 105A and 105B that pivotally connect two arms 106A and 106B to the drive shaft 102. The arms 106A and 106B are mounted so that they may pivot in planes tangential to the drive shaft at hinges 105A and 105B. In other words, if each arm 106A and 106B were to pivot around a line, each line would be perpendicular to the drive shaft rotation axis and would intersect the drive shaft rotation axis.

Note that in some applications, two hinges 105A and 105B are used at the distal end 104 of the drive shaft 102, and these hinges 105A and 105B are disposed on the exterior of the drive shaft 102, so that the interior of the drive shaft 102 may remain hollow and may accommodate a guide wire. In other applications, a single hinge may be used, which extends through the center of the drive shaft.

At the end of each arm 106A and 106B, at the end opposite the hinges 105A and 105B, each arm 106A and 106B attaches at a hinge 107A and 107B to an abrasive element 108A and 108B.

Each abrasive element 108A and 108B includes a cutting element 109A and 109B, which may cut, slice and/or scrape away a blockage when the drive shaft 102 is rotated in the "cutting" direction 24. In some applications, the cutting element 109A and 109B may be an edge of the abrasive element 108A and 108B, which may subtend an acute angle in cross-section. In other applications, the cutting element may be an actual blade that is attached to the abrasive element.

Each abrasive element 108A and 108B also includes a grinding element 110A and 110B, which may grind or sand away a blockage when the drive shaft 102 is rotated in the "grinding" direction 25. In some applications, the grinding element 110A and 110B may be an abrasive material disposed on the abrasive element 108A and 108B adjacent to and leading the cutting element 109A and 109B when the drive shaft 102 is rotated in the "grinding" direction 25. As used here, the term "leading" means that when the drive shaft 102 is rotated in the "grinding" direction 25, the grinding element 110A or 110B passes a particular point on the vessel just before the cutting element 109A or 109B. Similarly, when the drive shaft 102 is rotated in the "cutting" direction 24, the grinding element 110A or 110B passes a particular point on the vessel just after the cutting element 109A or 109B, and the grinding element is said to be trailing the cutting element when the drive shaft is rotated in the "cutting" direction 24.

In general, a single pass of the grinding or cutting elements over a blockage removes very little material from the blockage. Many passes are typically required to remove the full blockage. Because the drive shaft may be rotated very rapidly, typically over 100,000 revolutions per minute, many passes may be made in a reasonable amount of time.

The arms 106A and 106B and the abrasive elements 108A and 108B are forced radially outward when the drive shaft 102 is rotated at high speeds, in either direction. Such a force may arise from centrifugal force, and/or may arise from an external force delivered through the arms 106A and 106B.

Note that each abrasive element 108A and 108B has a largely planar face that contacts the blockage or the vessel wall. This face may be truly planar, or may have a slight curvature. In some applications, the face may be cylindrical, with a cylindrical axis that is parallel to the rotational axis of the drive shaft 102. In some applications, each cutting element 109A and 109B may be straight, or linear. In some applications, the face may be slightly convex along one dimension or along both dimensions.

Note also that the hinge mechanism that connects each abrasive element 108A and 108B to the respective arm 106A and 106B ensures that the largely planar face of the abrasive elements makes contact with the blockage or the vessel wall in at least two places. In some applications, such a geometry may reduce incidental damage to the vessel wall.

During insertion and positioning of the atherectomy device, prior to use, the arms 106A and 106B and the abrasive elements 108A and 108B are folded together to lie near the rotational axis of the drive shaft 102. In this folded position, these elements may have a relatively compact cross-section, and may fit inside the catheter 101. The optional taper 103 in the drive shaft may be used to accommodate all or a portion of the abrasive elements 108A and 108B to ensure that the abrasive elements 108A and 108B do indeed fit within the catheter 101.

The catheter may be used to position the abrasive elements at or near the blockage in the vessel. Once the device has been properly positioned, the drive shaft 102 is advanced past the distal end of the catheter 101, and/or the catheter 101 is retracted past the distal end of the abrasive elements 108A and 108B. This exposes the abrasive elements 108A and 108B to the blockage and/or the inside of the vessel.

Once the abrasive elements 108A and 108B are exposed, an optional spring may force the arms 106A and 106B apart from each other and away from the rotational axis of the drive shaft 102. Such a spring may be a compression spring that acts on one or both of the arms 106A and 106B, and/or may a torsional spring that acts through one or both hinges 105A and 105B to drive the arms 106A and 106B apart.

Alternatively, the spring or springs may be omitted, so that the arms 106A and 106B are not explicitly driven apart at low drive shaft rotational speeds or at rest. In these applications, the abrasive elements 108A and 108B may be driven apart only by centrifugal force, which forces them against the vessel wall and/or the blockage.

As a further alternative, there may be one or more biasing springs that force the arms 106A and 106B together, toward the rotational axis of the drive shaft, rather than force them apart. Such a biasing force may ensure that the arms 106A and 106B return to a folded position when the drive shaft rotation is completed, so that the abrasive elements 108A and 108B may be retracted into the catheter and may be easily removed from the vessel.

In alternate applications, more or fewer than two arms 106, hinges 105 and abrasive elements 108 may be used.

It is instructive to summarize the disclosure thus far. The atherectomy device disclosed herein has two important characteristics: (1) the atherectomy head is radially expandable beyond its rest size, and (2) the atherectomy head may be used for blockages having different hardness properties. The expandability arises from one or more arms on the head, each of which may extend away from the rotational axis of the drive shaft under the influence of centrifugal force and/or an external force applied to the arms. The effectiveness for different hardness blockages arises from having both a cutting element, which can remove soft blockage material, and a grinding element, which can remove hard blockage material. The drive shaft may be rotated in a "cutting" direction, thereby engaging the cutting element, or may be rotated in the opposite direction, known as a "grinding" direction, thereby engaging the grinding element. The cutting element may be an edge on an abrasive element, which may subtend an acute angle in cross-section and may therefore act like a blade. The grinding element may be an abrasive material disposed on the abrasive element adjacent to the cutting element, which may "lead" the cutting element when the drive shaft is rotated in the "grinding" direction. At a sufficiently high rotational velocity, centrifugal force may drive the one or more arms radially outward. It will be appreciated that the exact value for "sufficiently high" rotational velocity varies greatly from design to design, but the criterion for "sufficiently high" may be the rotational velocity at which centrifugal force is sufficient to force the one or more arms radially outward beyond the rest size of the atherectomy head.

In some applications, the atherectomy device uses a motor to rotate the drive shaft 20, which can operate in both directions. In some applications, the motor rotates the drive shaft with the same rotational velocity in both the cutting and grinding directions. In other applications, the motor rotates the drive shaft with different rotational velocities in the cutting and grinding directions. In still other applications, the rotation of the drive shaft is carried out by the user, rather than a motor. In these applications, the user may use a handle to rotate the drive shaft, or may optionally use a crank or other adapter to increase torque and/or increase the RPM of the user-initiated drive shaft rotation.

In some applications, the atherectomy device includes a valve that removes the debris that comes from the vessel wall. Such a valve may use a "trap door" or other suitable mechanism to trap the debris particles, and the device may use suitable plumbing to direct the trapped debris particles through the catheter and out of the vessel. In many cases, such a valve and/or plumbing system may be desirable, so that the debris particles do not cause vessel blockages downstream in smaller vessels.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

We claim:

1. A rotational atherectomy apparatus for abrading tissue, comprising:
    a flexible, elongated, rotatable drive shaft having a proximal end and a distal end opposite the proximal end, the drive shaft being rotatable in a cutting direction and in a grinding direction opposite the cutting direction; and
    an expandable atherectomy head disposed proximate the distal end of the drive shaft, the head rotatably expandable from a rest position with a rest diameter when not rotating to an expanded position with a rotational diameter when the drive shaft is rotated at a high rotational speed and due to centrifugal forces in both the cutting direction and the grinding direction, wherein the rotational diameter is greater than the rest diameter; the head comprising at least two arms that overlap the drive shaft and lie parallel thereto in the rest position and having free ends that extend away from the drive shaft in the expanded position due to the centrifugal forces generated during high speed rotation, each arm comprising an abrasive element comprising:
        a cutting element exposed to tissue in the expanded position when the drive shaft is rotated in the cutting direction at a high rotational speed; and
        a grinding element exposed to tissue in the expanded position when the drive shaft is rotated in the grinding direction at a high rotational speed.

2. The rotational atherectomy apparatus of claim 1, wherein the cutting element comprises an edge of the abrasive element.

3. The rotational atherectomy apparatus of claim 2, wherein the edge of the abrasive element has an acute angle in cross-section.

4. The rotational atherectomy apparatus of claim 1, wherein the grinding element comprises an abrasive material disposed on the abrasive element adjacent to the cutting element and leading the cutting element when the drive shaft is rotated in the grinding direction.

5. The rotational atherectomy apparatus of claim 1, wherein the arm includes a free end, the cutting element being attached to the free end of the arm.

6. The rotational atherectomy apparatus of claim 1, wherein the arm is pivotally attached to the drive shaft at an attachment point on the drive shaft and is pivotable in a plane tangential to the drive shaft at the attachment point.

7. The rotational atherectomy apparatus of claim 1, wherein the arm is hingedly attached to the drive shaft at an attachment point on the drive shaft and is pivotable in a plane that includes a rotational axis of the drive shaft.

8. The rotational atherectomy apparatus of claim 1, wherein the drive shaft includes an abrasive material disposed on its distal end.

9. The rotational atherectomy apparatus of claim 1, further comprising a valve for removing abraded debris.

10. A rotational atherectomy apparatus, comprising:
a flexible, elongated, rotatable drive shaft having a proximal end and a distal end opposite the proximal end, the drive shaft being rotatable in a cutting direction and in a grinding direction opposite the cutting direction; and
an expandable atherectomy head disposed proximate the distal end of the drive shaft, the head rotatably expandable from a rest position with a rest diameter when not rotating to an expanded position with a rotational diameter when the drive shaft is rotated at a high rotational speed and due to centrifugal forces in both the cutting direction and the grinding direction, wherein the rotational diameter is greater than the rest diameter, the head comprising:
a first arm pivotally attached to the drive shaft at a first drive shaft anchor point near the distal end of the drive shaft, the first arm being pivotable in a first plane tangential to the drive shaft at the first drive shaft anchor point and from the rest position to the expanded position due to centrifugal forces generated;
the first arm having a first arm free end that leads the first drive shaft anchor point when the drive shaft is rotated in the cutting direction and trails the first drive shaft anchor point when the drive shaft is rotated in the grinding direction;
the first arm free end having a first cutting feature on a leading edge of the first arm free end as the drive shaft is rotated in the cutting direction;
the first arm free end having a first grinding feature adjacent to the first cutting feature and leading the first cutting feature as the drive shaft is rotated in the grinding direction.

11. The rotational atherectomy apparatus of claim 10, wherein the first cutting feature is an edge having an acute angle in cross-section;
wherein the first grinding feature is an abrasive material disposed on the first arm free end adjacent to the first cutting feature.

12. The rotational atherectomy apparatus of claim 10, the head further comprising:
a second arm pivotally attached to the drive shaft at a second drive shaft anchor point near the distal end of the drive shaft, the second arm being pivotable in a second plane tangential to the drive shaft at the second drive shaft anchor point and from the rest position to the expanded position due to centrifugal forces generated;
the second arm having a second arm free end that leads the second drive shaft anchor point when the drive shaft is rotated in the cutting direction and trails the second drive shaft anchor point when the drive shaft is rotated in the grinding direction;
the second arm free end having a second cutting feature on a leading edge of the second arm free end as the drive shaft is rotated in the cutting direction; and
the second arm free end having a second grinding feature adjacent to the second cutting feature and leading the second cutting feature as the drive shaft is rotated in the grinding direction.

13. The rotational atherectomy apparatus of claim 12, wherein the first and second drive shaft anchor points are equidistant from the distal end of the drive shaft;
wherein the first and second drive shaft anchor points are on opposite sides of the drive shaft; and
wherein the first and second planes are parallel.

14. The rotational atherectomy apparatus of claim 12, wherein the first and second cutting features are edges, each edge having an acute angle in cross-section; and
wherein the first and second grinding features are abrasive material disposed on the first and second arm free ends, respectively, adjacent to the first and second cutting features, respectively.

15. The rotational atherectomy apparatus of claim 12, wherein the first and second arms have a combined center of mass that is generally coincident with a rotational axis of the drive shaft.

16. The rotational atherectomy apparatus of claim 12, wherein the first and second arms have a combined center of mass that is laterally displaced from a rotational axis of the drive shaft.

17. The rotational atherectomy apparatus of claim 10, wherein the first arm is substantially parallel to the drive shaft when the drive shaft is at rest.

18. The rotational atherectomy apparatus of claim 10, wherein the first arm is limited from extending completely perpendicular to the drive shaft when the drive shaft is at rotated at high speeds.

19. The rotational atherectomy apparatus of claim 10, further comprising a valve for removing abraded debris.

20. A rotational atherectomy apparatus, comprising:
a flexible, elongated, rotatable drive shaft having a proximal end and a distal end opposite the proximal end, the drive shaft being rotatable in a cutting direction and in a grinding direction opposite the cutting direction; and
an expandable atherectomy head disposed proximate the distal end of the drive shaft, the head rotatably expandable from a rest position with a rest diameter when not rotating to an expanded position with a rotational diameter when the drive shaft is rotated at a high rotational speed and due to centrifugal forces in both the cutting direction and the grinding direction, wherein the rotational diameter is greater than the rest diameter, the head comprising:
a first arm hingedly attached to the drive shaft at a first drive shaft anchor point near the distal end of the drive shaft, the first arm being pivotable in a first plane that includes a rotational axis of the drive shaft;
the first arm having a first arm free end that extends radially away from the drive shaft and from the rest position to the expanded position due to centrifugal forces generated at high drive shaft rotational speeds;

the first arm free end having a first cutting feature on a leading edge of the first arm free end as the drive shaft is rotated in the cutting direction; and the first arm free end having a first grinding feature adjacent to the first cutting feature and leading the first cutting feature as the drive shaft is rotated in the grinding direction.

21. The rotational atherectomy apparatus of claim 20, wherein the first cutting feature is an edge having an acute angle in cross-section;

wherein the first grinding feature is an abrasive material disposed on the first arm free end adjacent to the first cutting feature.

22. The rotational atherectomy apparatus of claim 20, further comprising:

a second arm hingedly attached to the drive shaft at a second drive shaft anchor point near the distal end of the drive shaft, the second arm being pivotable in a second plane that includes a rotational axis of the drive shaft;

the second arm having a second arm free end that extends radially away from the drive shaft and from the rest position to the expanded position due to centrifugal forces generated at high drive shaft rotational speeds;

the second arm free end having a second cutting feature on a leading edge of the second arm free end as the drive shaft is rotated in the cutting direction; and the second arm free end having a second grinding feature adjacent to the second cutting feature and leading the second cutting feature as the drive shaft is rotated in the grinding direction.

23. The rotational atherectomy apparatus of claim 22, wherein the first and second drive shaft anchor points are equidistant from the distal end of the drive shaft;

wherein the first and second drive shaft anchor points are on opposite sides of the drive shaft; and wherein the first and second planes are coincident.

24. The rotational atherectomy apparatus of claim 22, wherein the first and second cutting features are edges, each edge having an acute angle in cross-section; and wherein the first and second grinding features are abrasive material disposed on the first and second arm free ends, respectively, adjacent to the first and second cutting features, respectively.

25. The rotational atherectomy apparatus of claim 22, wherein the first and second arms have a combined center of mass that is generally coincident with a rotational axis of the drive shaft.

26. The rotational atherectomy apparatus of claim 22, wherein the first and second arms have a combined center of mass that is laterally displaced from a rotational axis of the drive shaft.

27. The rotational atherectomy apparatus of claim 20, further comprising a valve for removing abraded debris.

* * * * *